(12) United States Patent
Tsai et al.

(10) Patent No.: US 7,528,791 B2
(45) Date of Patent: May 5, 2009

(54) ANTENNA STRUCTURE HAVING A FEED ELEMENT FORMED ON AN OPPOSITE SURFACE OF A SUBSTRATE FROM A GROUND PORTION AND A RADIATING ELEMENT

(75) Inventors: Feng-Chi Eddie Tsai, Taipei Hsien (TW); Chia-Tien Li, Taipei Hsien (TW)

(73) Assignee: Wistron NeWeb Corporation, Taipei Hsien (TW)

( * ) Notice: Subject to any disclaimer, the term of this patent is extended or adjusted under 35 U.S.C. 154(b) by 62 days.

(21) Appl. No.: 11/457,461

(22) Filed: Jul. 14, 2006

(65) Prior Publication Data
US 2007/0030203 A1 Feb. 8, 2007

Related U.S. Application Data

(63) Continuation-in-part of application No. 11/164,364, filed on Nov. 21, 2005.

(30) Foreign Application Priority Data
Aug. 8, 2005 (TW) .............................. 94126825 A

(51) Int. Cl.
*H01Q 1/48* (2006.01)
*H01Q 1/38* (2006.01)
*H01Q 1/24* (2006.01)

(52) U.S. Cl. .............................. 343/846; 343/700 MS; 343/702

(58) Field of Classification Search .......... 343/700 MS, 343/702, 846
See application file for complete search history.

(56) References Cited

U.S. PATENT DOCUMENTS 6,320,545 B1 11/2001 Nagumo (Continued)

FOREIGN PATENT DOCUMENTS

TW 1220581 3/2003

(Continued)

OTHER PUBLICATIONS

Printed Dual-Band U-Slotted Monopole Antenna for WLAN Access Point (MOTL_V38-I06_p436-438.pdf).

(Continued)

*Primary Examiner*—Hoang V Nguyen
*Assistant Examiner*—Robert Karacsony
(74) *Attorney, Agent, or Firm*—Winston Hsu

(57) ABSTRACT

An antenna includes a substrate, a ground element, a radiating element and a feed element. The ground element is disposed on the substrate and has an opening. The radiating element is disposed on the substrate and electrically connects to the ground element. The radiating element comprises a first radiating trace and a second radiating trace. The first radiating trace includes a first segment, a second segment, and a first bended portion connected the first segment and the second segment. The second radiating trace connects to the second segment of the first radiating trace. The feed element is disposed on the substrate and electrically connects to the radiating element. The feed element and the radiating element are at the same surface of the substrate, and a part of the feed element extends and enters the opening.

11 Claims, 13 Drawing Sheets

U.S. PATENT DOCUMENTS

| | | |
|---|---|---|
| 6,459,413 B1 | 10/2002 | Tseng et al. |
| 6,809,689 B1 * | 10/2004 | Chen .................. 343/700 MS |
| 6,861,986 B2 | 3/2005 | Fang et al. |
| 6,985,114 B2 | 1/2006 | Egashira |
| 6,995,714 B2 | 2/2006 | Sim |
| 2004/0090377 A1 | 5/2004 | Dai |
| 2004/0178957 A1 | 9/2004 | Chang |
| 2004/0207557 A1 | 10/2004 | Chen |
| 2006/0109192 A1 * | 5/2006 | Weigand ..................... 343/795 |
| 2007/0229358 A1 * | 10/2007 | Chi et al. ............. 343/700 MS |
| 2007/0296636 A1 * | 12/2007 | Lee ........................... 343/702 |

FOREIGN PATENT DOCUMENTS

| | | |
|---|---|---|
| TW | 542419 | 7/2003 |
| TW | 583783 | 4/2004 |

OTHER PUBLICATIONS

Compact Triple-Band Planar Inverted-F Antenna for Mobile Handsets (MOTL_V41-I06_p483-486.pdf).

* cited by examiner

ANTENNA STRUCTURE HAVING A FEED ELEMENT FORMED ON AN OPPOSITE SURFACE OF A SUBSTRATE FROM A GROUND PORTION AND A RADIATING ELEMENT

CROSS REFERENCE TO RELATED APPLICATIONS

This application is a Continuation-In-Part of U.S. patent application Ser. No. 11/164,364 entitled "Antenna Structure," filed Nov. 21, 2005, the contents of which are incorporated by reference herein.

BACKGROUND OF THE INVENTION

1. Field of the Invention

The invention provides an antenna, and more specifically, a multi-frequency antenna.

2. Description of the Prior Art

In the prior art, an inverted F antenna is usually used to realize a radio signal switch. As those skilled in the art know, the basic inverted F antenna includes a radiating element. One end of the radiating element connects with a ground element, and the middle of the radiating element is used as the feeding point of the signal. The ground element and the signal feeding point form two transverse portions of an F shape (The radiating element becomes the back of the F shape.). The length of the antenna has a relationship with a radiating frequency of transmitting and receiving. However, the simple inverted F antenna only supports a single-frequency for transmitting and receiving radio signals. It cannot integrate multiple frequencies for transmitting and receiving radio signals. The length of the radiating element is relatively long, so compact size requirements of the information industry cannot be met. In addition, U.S. Pat. No. 6,861,986 provides a kind of multiple-frequency application for an inverted F antenna. However, the antenna uses two ends in a straight line radiating element to radiate two frequencies. Thus, the size of the radiating element is not compact.

SUMMARY OF THE INVENTION

It is therefore a objective of the claimed invention to provide a multiple-frequency antenna that can not only support multiple-frequency transmitting and receiving of radio signals, but also has compact size without having an effect on the performance of antenna.

An embodiment of the invention provides an antenna comprising a substrate, a ground element, a radiating element and a feed element. The ground element is disposed on the substrate and has an opening. The radiating element is disposed on the substrate and electrically connects to the ground element. The radiating element has a first radiating trace and a second radiating trace. The first radiating trace includes a first segment, a second segment, and a first bended portion connecting the first segment and the second segment. The second radiating trace connects to the second segment of the first radiating trace. The feed element is disposed on the substrate and electrically connects to the radiating element. The feed element and the radiating element are at the same surface of the substrate, and a part of the feed element extends and enters the opening.

An embodiment of the invention further provides an antenna comprising a substrate, a ground element, a radiating element and a feed element. The substrate has a first surface and a second surface. The ground element is disposed on the first surface and has an opening. The radiating element is disposed on the first surface and electrically connects to the ground element. The radiating element comprises a first radiating trace and a second radiating trace. The first radiating trace includes a first segment, a second segment and a first bended portion connected the first segment and the second segment. The second radiating trace connects to the second segment of the first radiating trace. The feed element is disposed on the second surface and electrically connects to the radiating element. A projection of the feed element on the first surface partially overlaps the opening.

An embodiment of the invention further provides an antenna comprising a substrate, a ground element, a radiating element and a feed element. The ground element is disposed on the substrate and has an opening. The radiating element is disposed on the substrate and electrically connects to the ground element. The feed element is disposed on the substrate and electrically connects to the radiating element. The feed element and the radiating element are at the same surface of the substrate, and a part of the feed element extends and enters the opening.

An embodiment of the invention further provides an antenna comprising a substrate, a ground element, a radiating element and a feed element. The substrate has a first surface and a second surface. The ground element is disposed on the first surface and has an opening. The radiating element is disposed on the first surface and electrically connects to the ground element. The feed element is disposed on the second surface and electrically connects to the radiating element. A projection of the feed element on the first surface partially overlaps the opening.

An embodiment of the invention further provides an electronic device comprising a case and an antenna. The antenna is disposed in the case. The antenna comprises a substrate, a ground element, a radiating element and a feed element. The ground element is disposed on the substrate and has an opening. The radiating element is disposed on the substrate and electrically connects to the ground element. The feed element is disposed on the substrate and electrically connects to the radiating element. The feed element and the radiating element are at the same surface of the substrate, and a part of the feed element extends and enters the opening.

An embodiment of the invention further provides an electronic device comprising a case and an antenna. The antenna is disposed in the case. The antenna comprises a substrate, a ground element, a radiating element and a feed element. The substrate has a first surface and a second surface. The ground element is disposed on the first surface and has an opening. The radiating element is disposed on the first surface and electrically connects to the ground element. The feed element is disposed on the second surface and electrically connects to the radiating element. A projection of the feed element on the first surface partially overlaps the opening.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
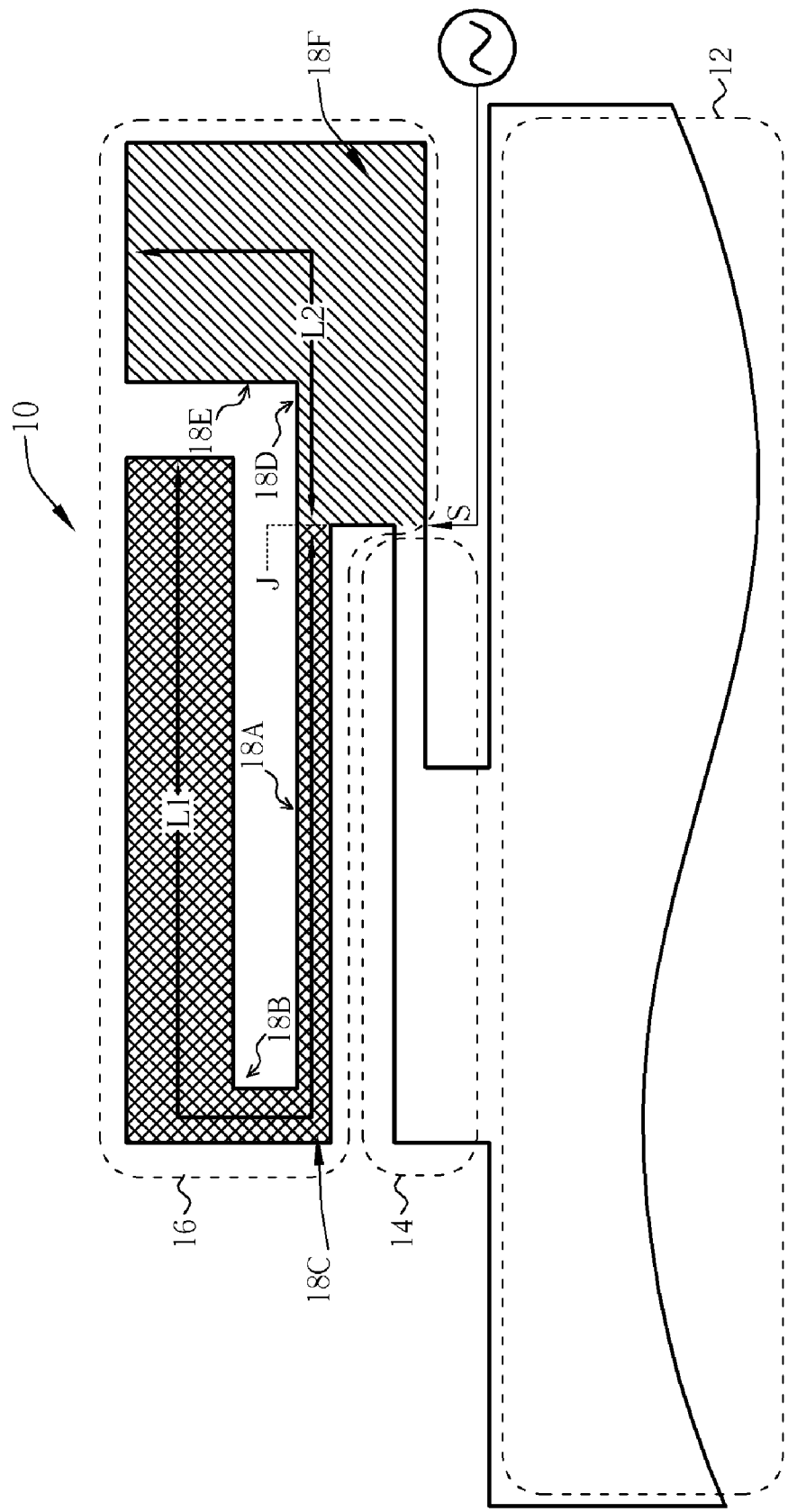
FIGS. 1 to 8 are schematic diagrams of a plurality of antennas of embodiments of the invention.

FIG. 1 shows an embodiment of the antenna 10 according to the invention. The antenna 10 includes a ground element 12, an interconnecting element 14, and a radiating element 16. Each component can be formed by an electrically conductive surface, for example, by a conductive layer in a printed circuit board. As shown in FIG. 1, the ground element 12 is used to connect with the ground, and the radiating element 16 and the ground element 12 are separated but mutually connected by the interconnecting element 14 disposed between. The radiating element 16 is divided into two radiating traces in which a crosshatched region is a first radiating trace L1, and a single-hatched region is a second radiating trace L2. The two radiating traces L1 and L2 use the interconnecting element 14 to connect with the ground element 12. In this embodiment, the interconnecting element 14 has two bent segments, so the signal can input to and output from the antenna 10 by one feeding point S of signals. In other words, a signal line is connected to the feeding point S. In FIG. 1, the two radiating traces L1 and L2 of the radiating element 16 both have bends. In the first radiating trace L1, the region parallel with the ground element 12 is a first segment 18A, and the region extending above along a bended portion 18C is a second segment 18B. Similarly, in the second radiating trace L2, the portion parallel to the ground element 12 is a third segment 18D, and the portion extending above along a bended portion 18F is a fourth segment 18E. Owing to the bent shape design of the radiating element of the embodiment of the invention, the size and the occupied volume of the radiating element is compact and efficient.

As FIG. 1 shows, based on the interconnecting portion J, the antenna 10 can resonate two different frequencies by means of the left element and the right element of the radiating element, and the antenna 10 of the embodiment of the invention can integrate the transmitting and receiving of signals. When fabricating the antenna 10, the operating frequencies of the antenna 10 can be adjusted by changing the lengths of the radiating traces L1 and L2. From FIG. 1, we can see that the radiating traces L1 and L2 are bent in reverse directions, so that the embodiment of the invention has compact size radiating elements.

Figure 2:
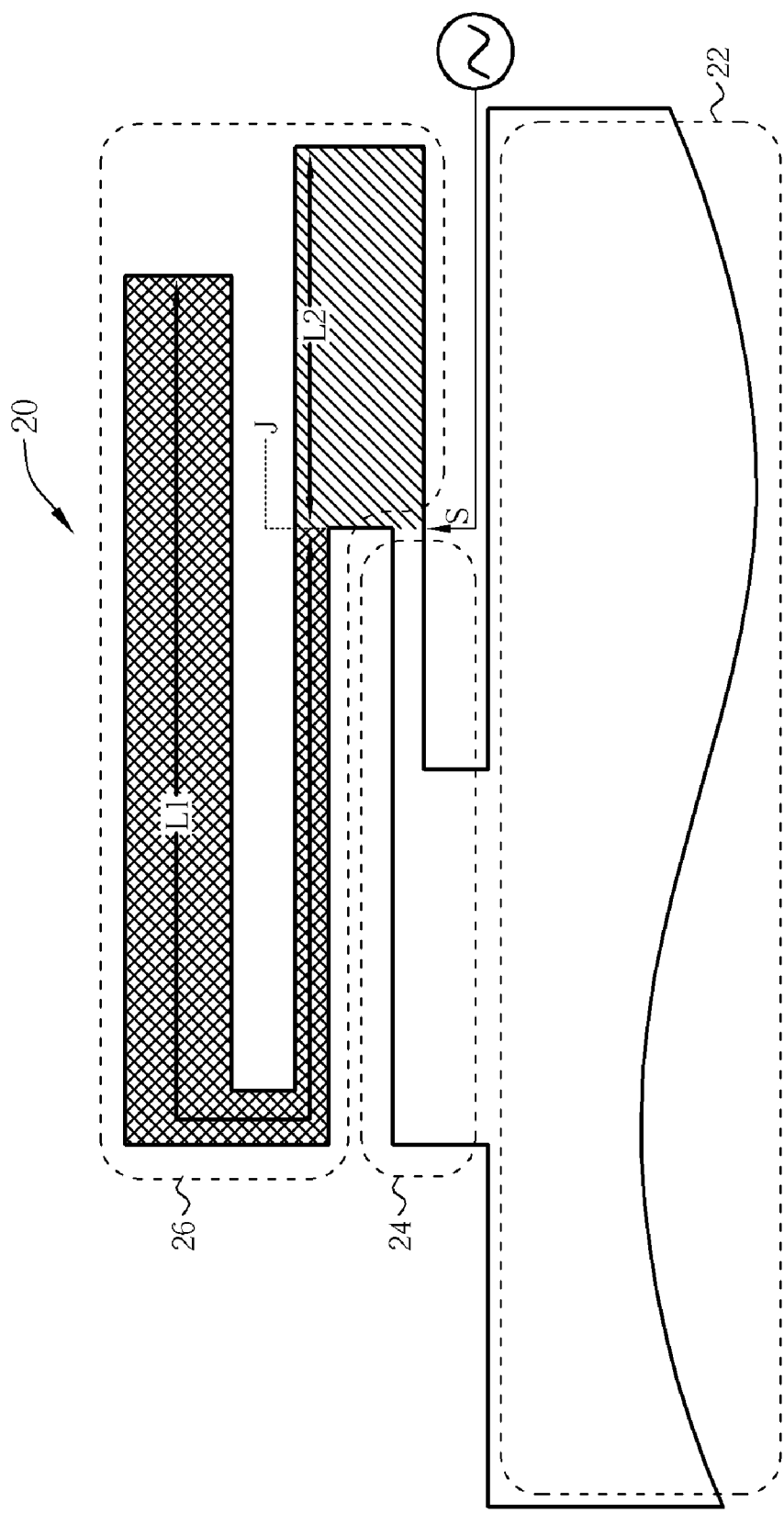

In the embodiment of FIG. 1, the two radiating traces L1 and L2 of the radiating element 16 both have bent structure. However, another embodiment of the invention also provides an antenna 20 with one radiating trace bent, as shown in FIG. 2. Similar to the antenna 10 of FIG. 1, the antenna 20 of FIG. 2 also has ground element 22, a bent interconnecting element 24, and a radiating element 26. But only the left radiating trace L1 (cross-hatched portion) of the antenna 20 forms a reverse-bent structure, the right radiating trace L2 (single-hatched portion) has a segment paralleling to the ground element. The straight portion still has the effect of resonating, and the antenna 20 can resonate two frequencies.

In the embodiment of FIG. 1, the first radiating trace L1 of the first radiating element 16 is bent into two sub-segments. However, according to the invention, each radiating trace can have more bended portions. Please refer to the embodiment of FIG. 3, which shows an antenna 30. Similar to the antenna 10 of FIG. 1, the antenna 30 also has a ground element 32, an interconnecting element 34, and a radiating element 36. However, in the left radiating trace L1 (cross-hatched portion), a first element 38 is divided into four segments by three turning points. As FIG. 1 shows, the antenna 30 can radiate two kinds of different frequencies with radiating traces L1 and L2.

Figure 3:
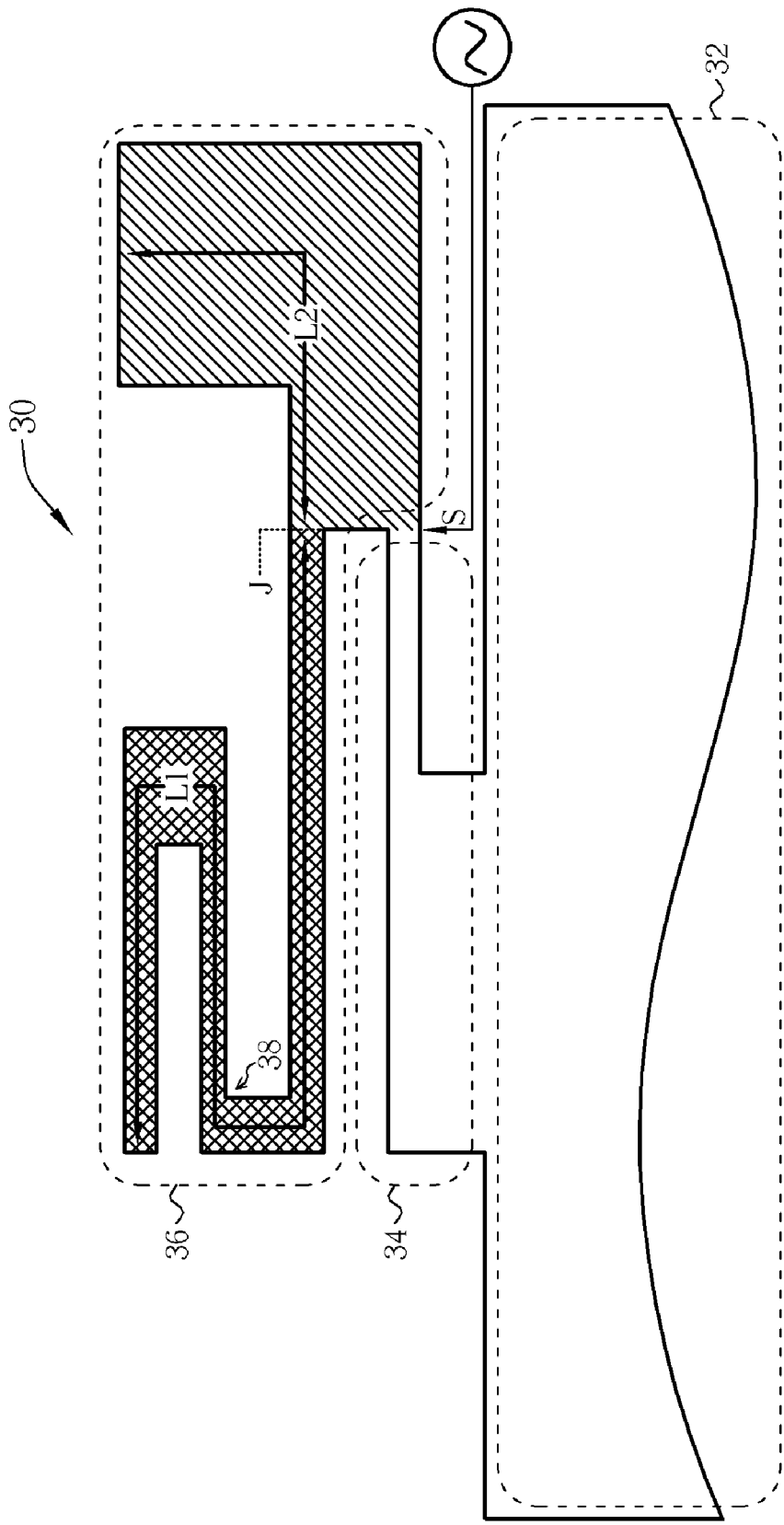

In the embodiments of FIG. 1 to FIG. 3, each segment is extending in an up direction, and is not extending in a down direction between a radiating element and ground element. Besides, a width of each segment can be different. For example, in the embodiment of FIG. 1, the width of the segment 18D is larger than the width of the segment 18E. According to simulation and test, the antennas of FIG. 1 to FIG. 3 of the invention can achieve omni-directional radiating field patterns, and have good bandwidth in the two radiating frequencies.

Figure 4:
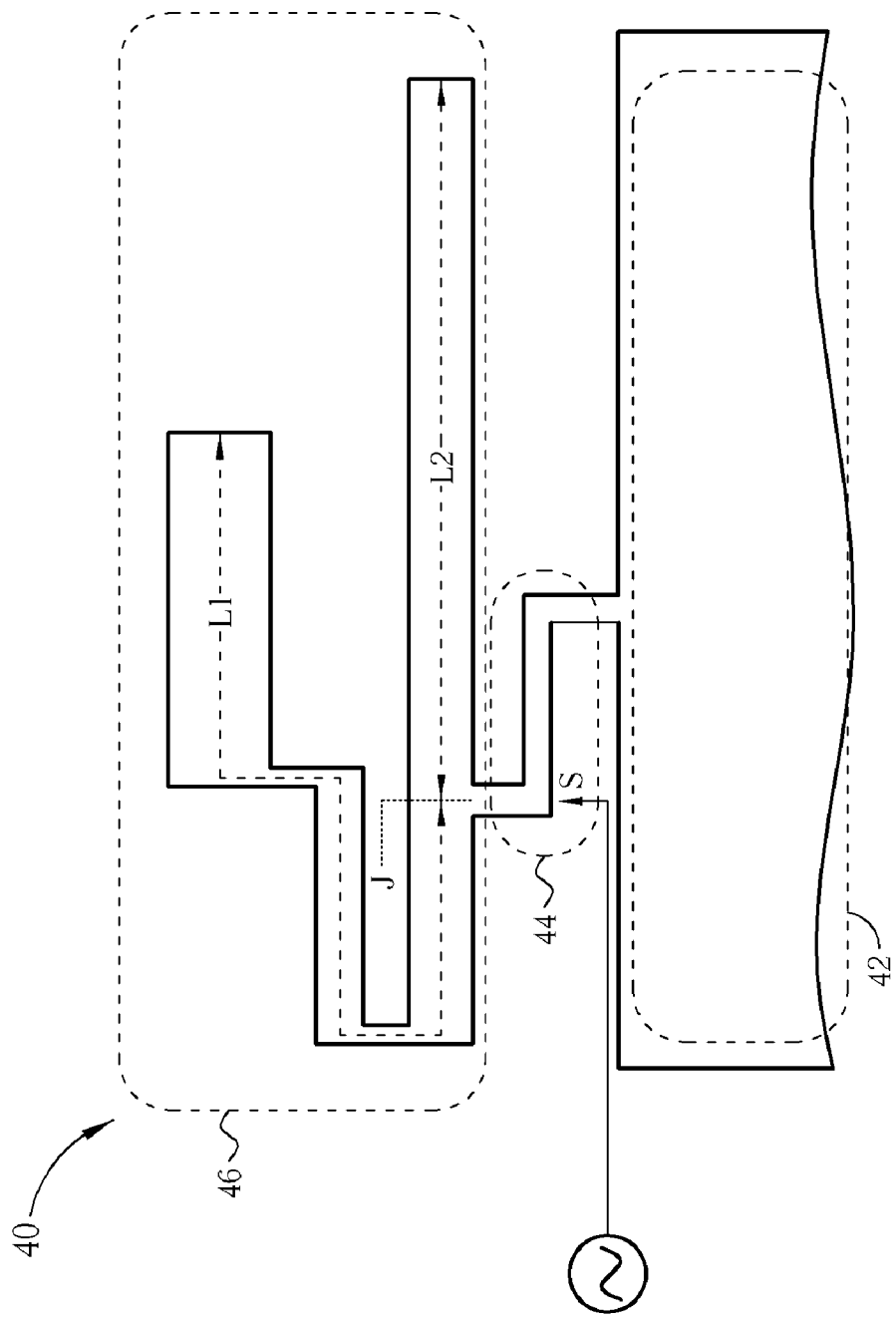

FIG. 4 shows another embodiment 40 of an antenna of the present invention. An antenna 40 includes a ground element 42, an interconnecting element 44 and a radiating element 46. In this embodiment, the interconnecting element is bent into three segments by two turning points. The signal of a transmission line can be fed in from a feeding line. Based on an interconnecting portion J, the radiating element 48 can resonate two different frequencies by means of the left element L1 and the right element L2 of the radiating element 48.

Figure 5:
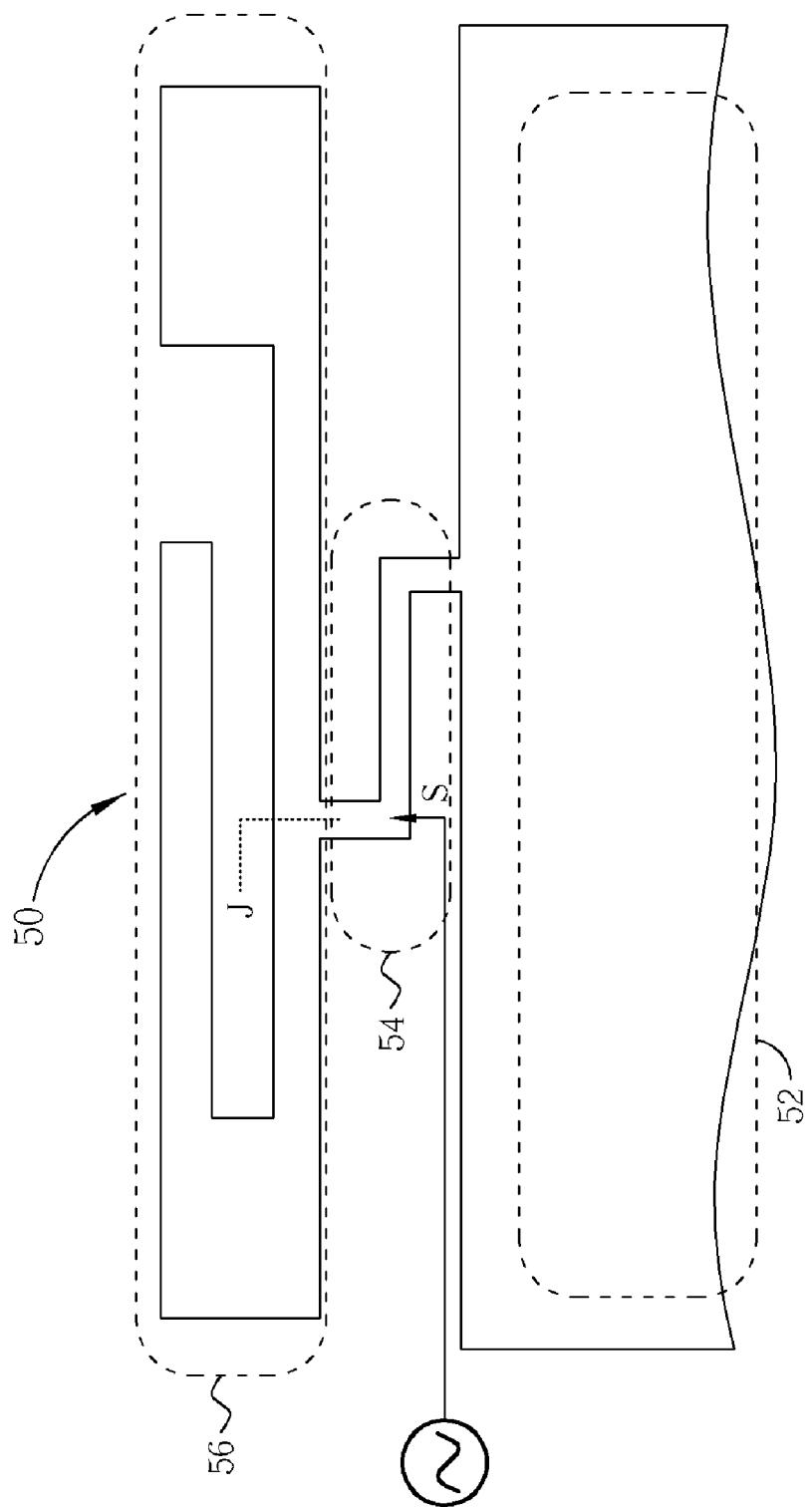
Figure 6:
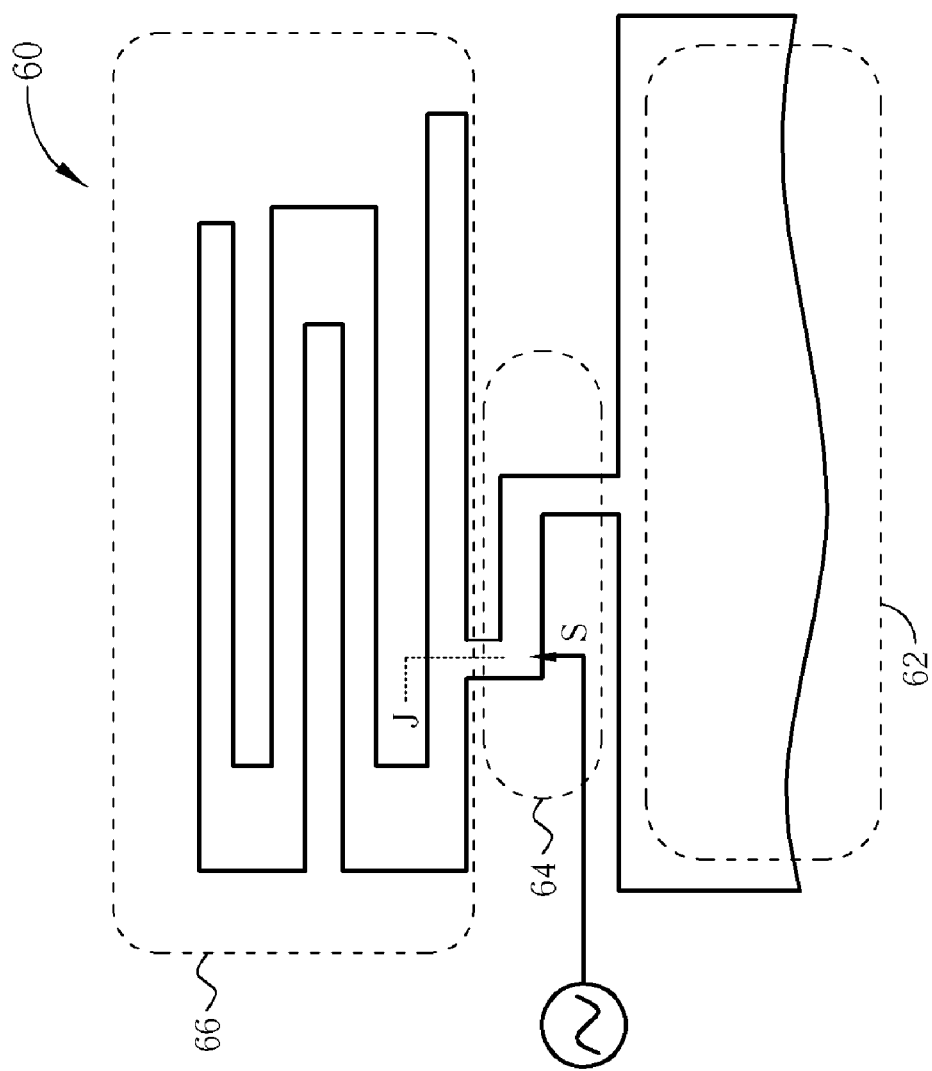

FIGS. 5 and 6 show two embodiments. Similar to the antenna 40 of FIG. 4, an antenna 50 of FIG. 5 includes a ground element 52, an interconnecting element 54, and a radiating element 56. The two radiating traces of the radiating element 58 both have bended portions. An antenna 60 of FIG. 6 includes a ground element 62, an interconnecting element 64 and a radiating element 66. The left radiating trace of the radiating element 66 has a plurality of turning points to subdivide the left radiating trace into a plurality of segments.

Figure 7:
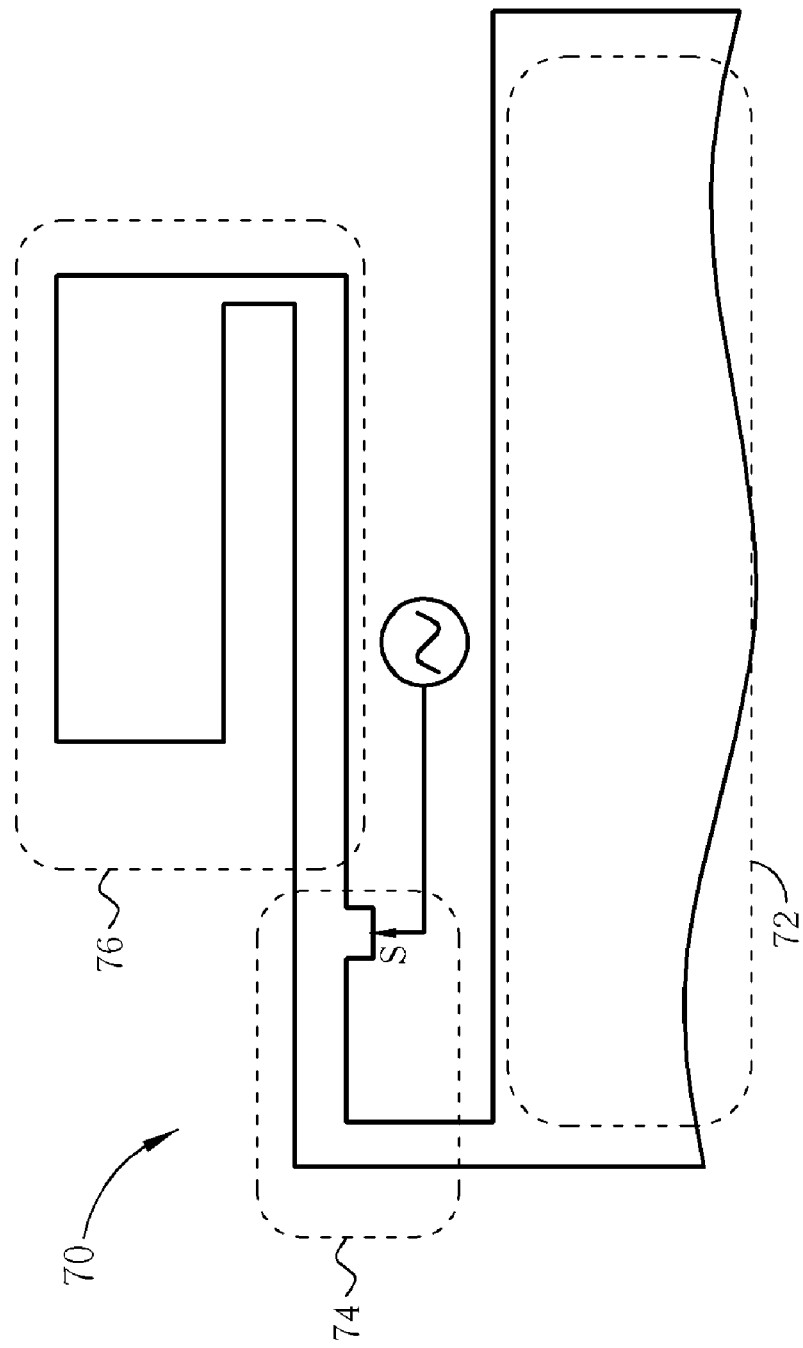

In FIG. 1 to FIG. 6, each antenna is designed for the aim of two frequencies. However, the spirit of the invention can also apply to a single-frequency inverted F antenna for reducing the size by way of bends. Regarding this kind of application, please refer FIG. 7, which shows an application of a single frequency antenna 60 of the invention. An antenna 70 includes a ground element 72, an interconnecting element 74 and a radiating element 76. The right portion of the radiating element 76 is bent for compacting the size of the radiating element 76.

According to the invention, a ground element, an interconnecting element, and a bent radiating element can be coplanar and, for example, formed in a printed circuit board. However, the antenna can also be of a three-dimensional and non-coplanar type.

In summary, the antenna of the present invention has a bent radiating element, which means that the radiating element is of compact size. Compared with the prior art, the antenna of the present invention can transmit and receive electromagnetic waves of multiple frequencies, has a compact size, has parameters that are not adversely influenced, achieves an omni-directional radiating field pattern, and has good bandwidth in each frequency.

Figure 8:
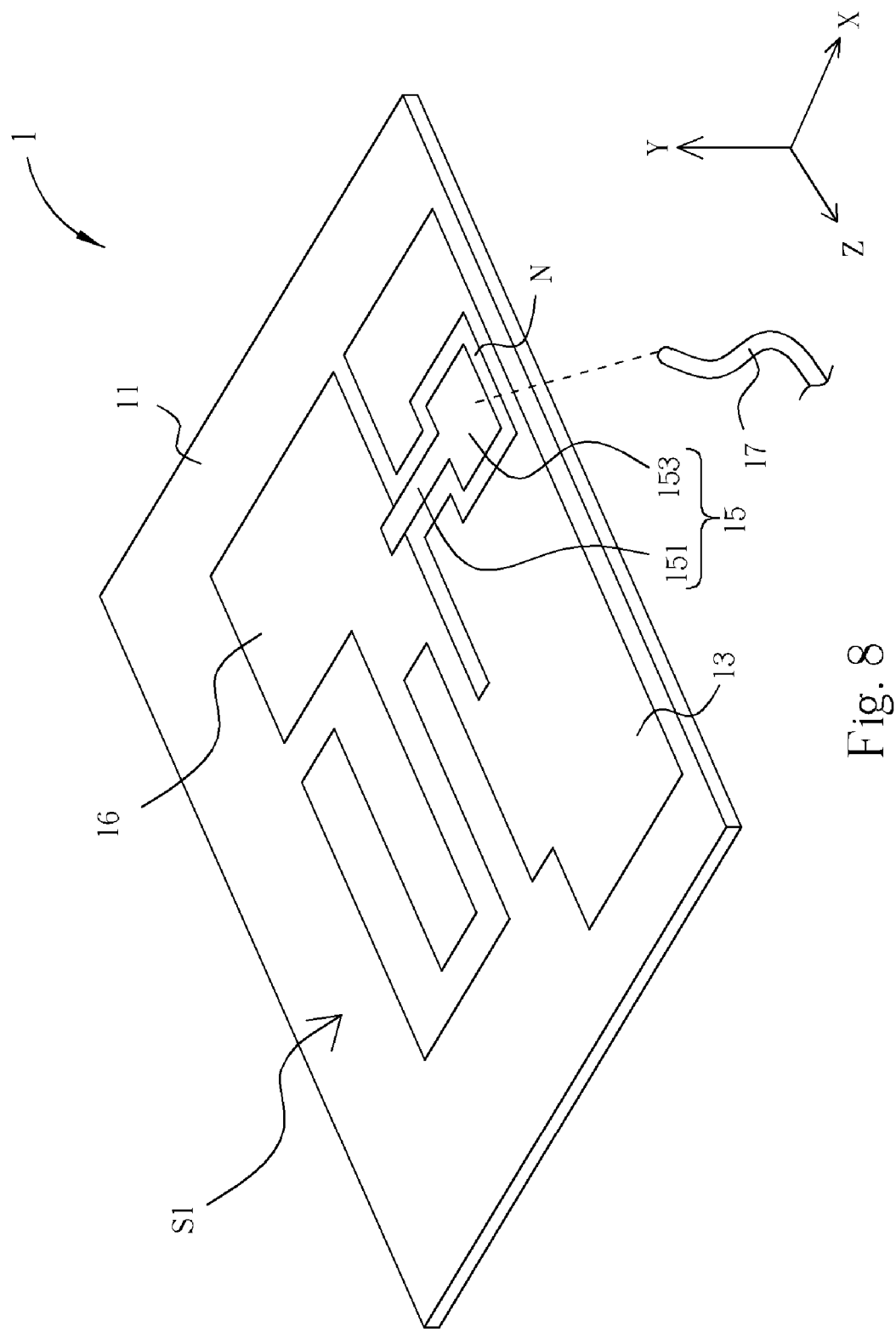

FIG. 8 shows another embodiment of an antenna 1 according to the invention. Similar to the antenna 10 in FIG. 1, the antenna 1 comprises a substrate 11, a ground element 13, a radiating element 16, a feed element 15 and cable 17. The substrate 11 has a first surface S1. The ground element 13 is disposed on the first surface S1 and has an opening N. An opening of the opening N faces toward the radiating element 16. The radiating element 16 is disposed on the first surface S1 and electrically connected to the ground element 13. The feed element 15 is disposed on the first surface S1 and electrically connected to the radiating element 16. A part of the feed element 15 extends and enters to the opening N, and comprises an extending signal line 151 and a feeding point 153. The extending signal line 151 connects the radiating element 16 and the feeding point 153, and enters the opening N substantially along the X-axis (first axis). The feeding point 153 is totally disposed inside the opening N. The cable 17 electrically connects to the feeding point 153 from the first surface S1 of the substrate 11 for transmitting signal.

In this embodiment, the profile of the opening N has is T shape, corresponds to the feed element 15, and arranges symmetrically according to the X-axis. The opening N separates from the feed element 15 a predetermined distance, for example, the distance between the opening N and the feed element 15 is at least half of the width of the extending signal line 151.

Figure 9:
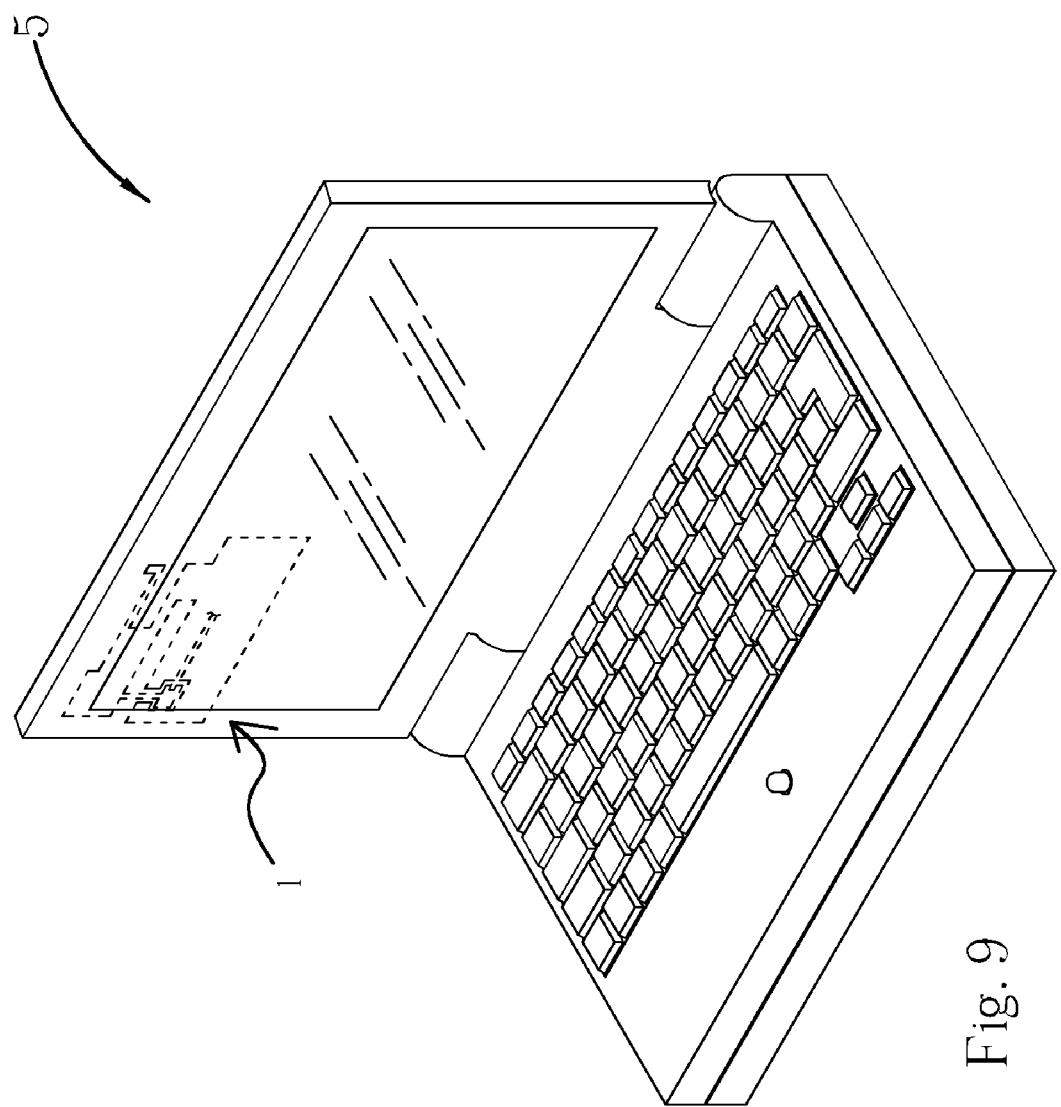
FIG. 9 is a schematic diagram of an antenna of an embodiment of the invention disposed in an electronic device.
Figure 10:
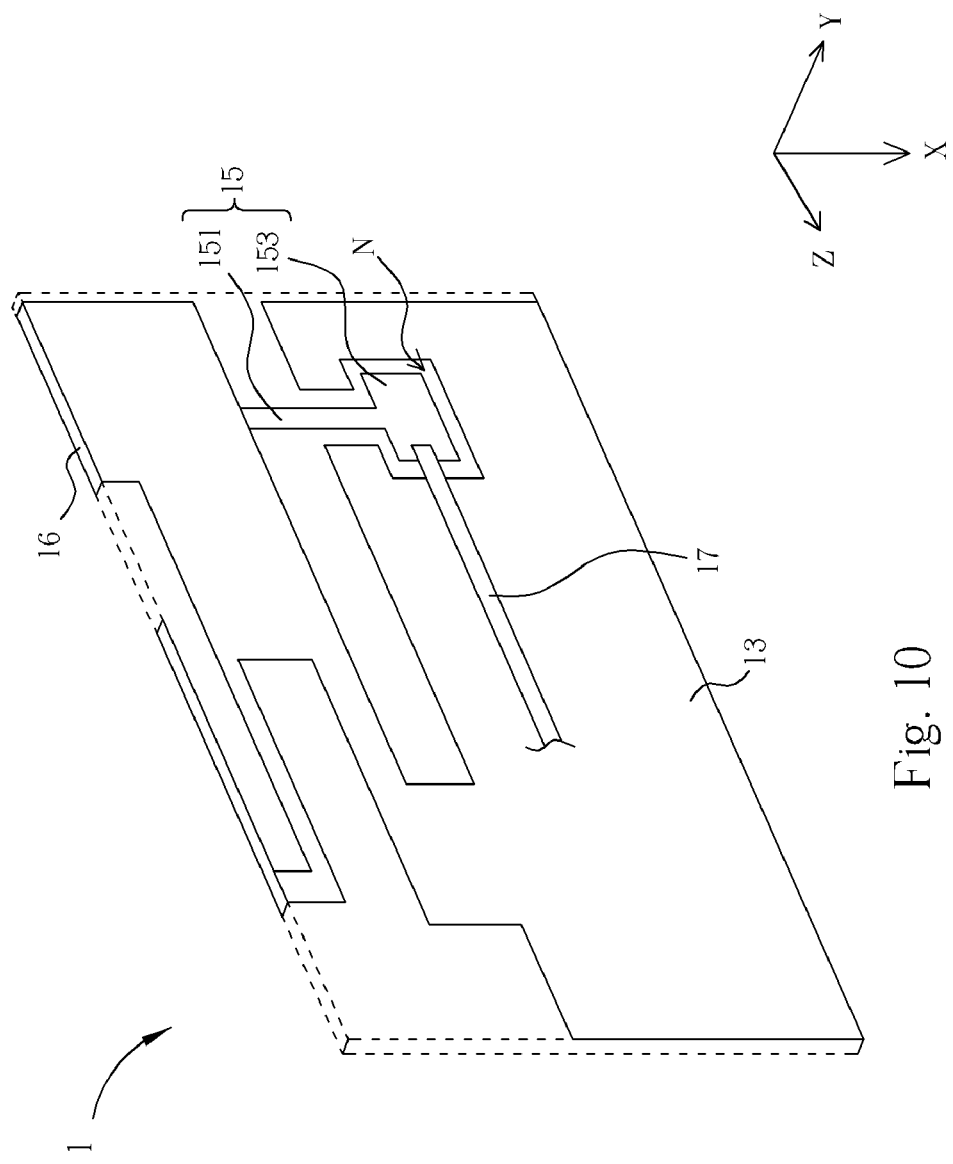
FIGS. 10 to 13 are schematic diagrams of a plurality of antennas of embodiments of the invention.

Referring to FIGS. 9 and 10, the antenna 1 of the invention is installed in a case of an electronic device (Notebook) 5, collapsed to form a 3D structure. As shown, the cable 17 connects to the feeding point 153 along the ground element 13 so that the cable 17 is not interfered by other structures in the electronic device and not to be bent for co-operating with the antenna 1.

Compared with the prior art, the connecting position of the cable 17 and the feeding point 153 is shifted downward along the X-axis into the opening N of the ground element 13. Thus, the feeding point 153 and the radiating element 16 are physically isolated, and it is convenient for the arrangement of the cable 17.

Figure 11:
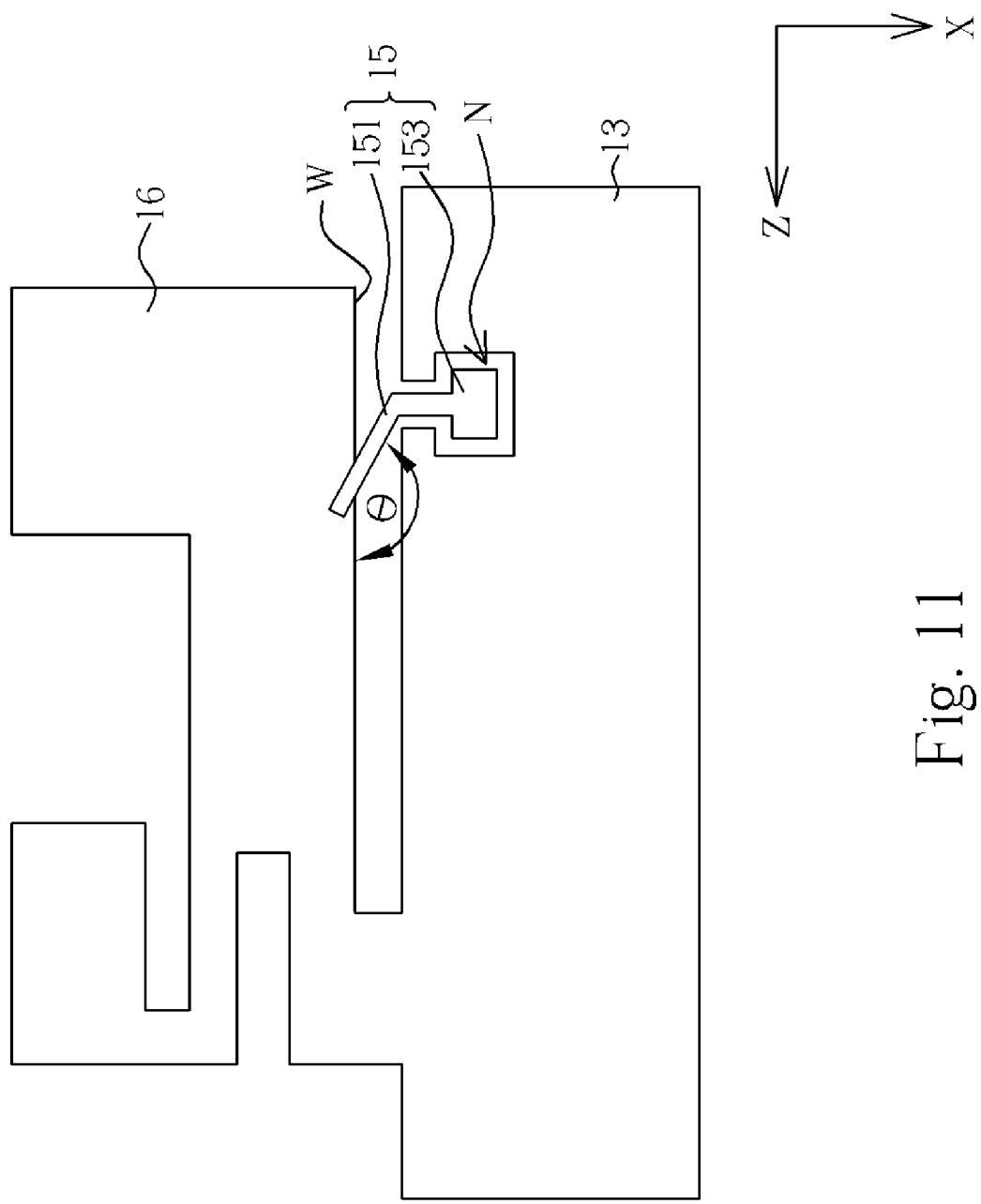

FIG. 11 shows a modification of the antenna 1 in FIG. 8. The feed element 15 connects to the radiating element 16 from a sidewall W thereof, so that an angle θ is formed therebetween. The range of the angle θ is about 90 degree to 180 degree.

Figure 12:
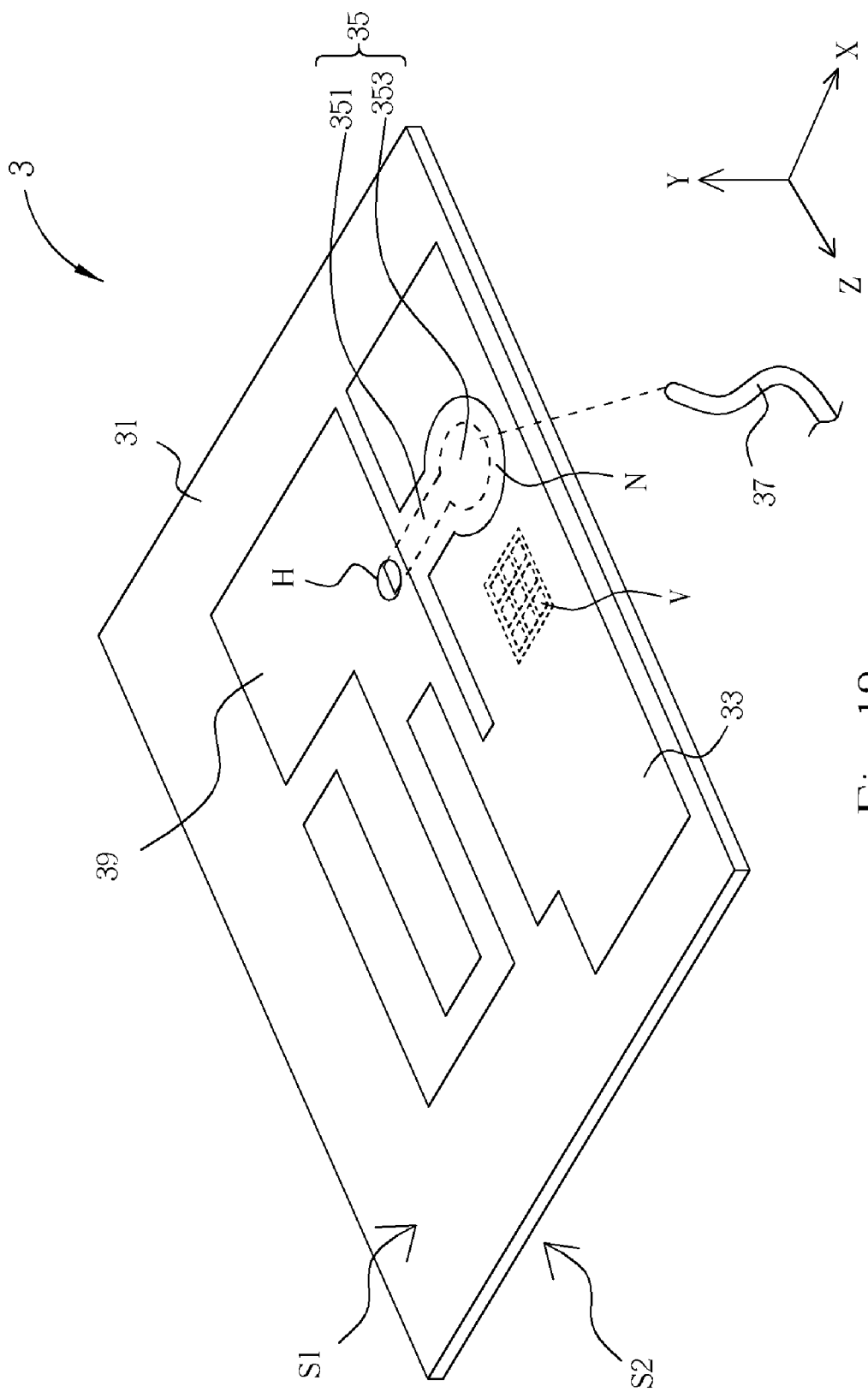
Figure 13:
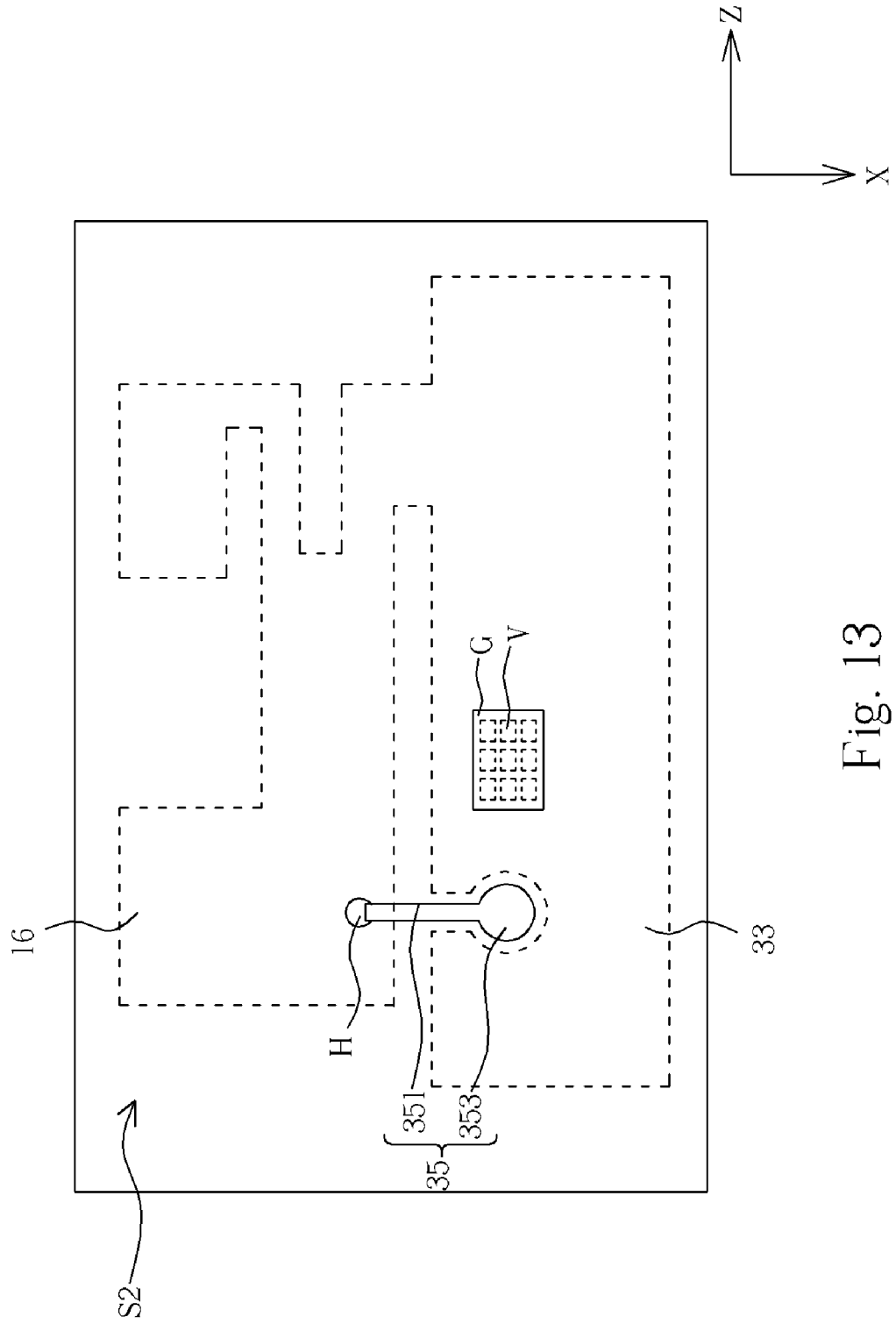

FIGS. 12 and 13 show another embodiment of an antenna 3 according to the invention. The antenna 3 comprises a substrate 31, a ground element 33, a radiating element 39, a feed element 35 and cable 37. The substrate 31 has a first surface S1 and a second S2 opposite to the first surface S1. The ground element 33 is disposed on the first surface S1 and has an opening N. An opening of the opening N faces toward the radiating element 39. The radiating element 39 is disposed on the first surface S1 and electrically connected to the ground element 33. The feed element 35 is disposed on the second surface S2 (shown in FIG. 13) and electrically connected to the radiating element 39 via a through hole H. The projection of the feed element 35 on the first surface S1 partially overlaps the opening N. The feed element 35 comprises an extending signal line 351 and a feeding point 353. The extending signal line 351 substantially extends along the X-axis (first axis) and connects the radiating element 39 and the feeding point 353. The projection of the feeding point 353 on the first surface S1 is totally inside the opening N. The cable 37 electrically connects to the feeding point 353 from the second surface S2 of the substrate 31 for transmitting signal.

The antenna 3 further comprises a ground part G disposed on the second surface S2 of the substrate 31. Several conductive holes V are between the ground part G and the ground element 33, so that the ground part G electrically connects to the ground element 33 via the conductive holes V. The cable 37 may be a coaxial cable with outer coaxial braid shield. The outer coaxial braid shield of the cable 37 connects to the ground element 33 via the ground part G and the conductive holes V.

In this embodiment, the profile of the opening N has is a U shape, corresponds to the feed element 35, and arranges symmetrically according to the X-axis. The opening N separates from the projection of the feed element 35 on the first surface S1 a predetermined distance, for example, the distance between the opening N and the feed element 35 is at least half of the width of the extending signal line 351.

Compared with the prior art, the connecting position of the cable 37 and the feeding point 353 is shifted downward along the X-axis into the opening N of the ground element 33. The radiating element 39 and the feeding point 353 are respectively disposed on the first surface S1 and the second surface S2. Thus, the feeding point 353 and the radiating element 39 are physically isolated, and it is convenient for the arrangement of the cable 37.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An antenna comprising:
    a substrate having a first surface and a second surface;
    a ground portion disposed on the first surface and having a recessed portion embedded in the ground portion at a depth to form an opening of an edge of the ground portion, wherein the recessed portion is opposite the opening of the edge of the ground portion, and the recessed portion is wider than the opening of the edge of the ground portion;
    a radiating element disposed on the first surface, electrically connected to the ground portion, and defining a through hole, the radiating element comprising:
        a first radiating trace including a first segment, a second segment and a first bended portion connecting the first segment and the second segment; and
        a second radiating trace connected to the second segment; and
    a feed element disposed on the second surface and electrically connected to the radiating element via the through hole of the radiating element on the substrate, wherein a projection of the feed element on the first surface partially overlaps the recessed portion.

2. The antenna of claim 1, wherein the second radiating trace comprises a third segment, a fourth segment and a second bended portion connected the third segment and the fourth segment.

3. An antenna comprising:
    a substrate having a first surface and a second surface;
    a ground portion disposed on the first surface and having a recessed portion embedded in the ground portion at a depth to form an opening of an edge of the ground portion, wherein the recessed portion is opposite the opening of the edge of the ground portion, and the recessed portion is wider than the opening of the edge of the ground portion;
    a radiating element disposed on the first surface, electrically connected to the ground portion, and defining a through hole; and
    a feed element disposed on the second surface and electrically connected to the radiating element via the through hole of the radiating element on the substrate, wherein a projection of the feed element on the first surface partially overlaps the recessed portion.

4. The antenna of claim 3, wherein the feed element connects the radiating element at a sidewall of the radiating element, an angle is formed between the feed element and the sidewall, and a range of the angle is between 90 degrees and 180 degrees inclusive.

5. The antenna of claim 3, wherein a projection of the feed element on the first surface enters the recessed portion along a first axis, and a profile of the recessed portion is symmetrical according to the first axis.

6. The antenna of claim 3, wherein the feed element comprises an extending signal line and a feeding point, the extending signal line connects the feeding point and the radiating element, and a projection of the feeding point on the first surface is disposed inside the recessed portion.

7. The antenna of claim 6, further comprising a cable electrically connected to the feeding point for transmitting radio signals.

8. The antenna of claim 7, further comprising a ground part disposed on the second surface of the substrate, a plurality of conductive holes is formed between the ground part and the ground portion so that the ground part electrically connects to the ground portion via the plurality of conductive holes.

9. The antenna of claim 8, wherein the cable comprises a coaxial cable with an outer coaxial braid shield, the outer coaxial braid shield electrically connects the ground part.

10. The antenna of claim 6, wherein a distance between the recessed portion and a projection of the feed element on the first surface is at least half of a width of the extending signal line.

11. An electronic device, comprising:
a case; and
an antenna disposed in the case, the antenna comprising:
a substrate having a first surface and a second surface;
a ground portion disposed on the first surface and having a recessed portion embedded in the ground portion at a depth to form an opening of an edge of the ground portion, wherein the recessed portion is opposite the opening of the edge of the ground portion, and the recessed portion is wider than the opening of the edge of the ground portion;
a radiating element disposed on the first surface, electrically connected to the ground portion, and defining a through hole; and
a feed element disposed on the second surface and electrically connected to the radiating element via the through hole of the radiating element on the substrate, wherein a projection of the feed element on the first surface partially overlaps the recessed portion.

* * * * *